United States Patent
Peltola et al.

(10) Patent No.: US 11,642,550 B2
(45) Date of Patent: May 9, 2023

(54) METHOD AND APPARATUS TO FACILITATE GENERATING AN OPTIMIZED RADIATION TREATMENT PLAN USING DIRECT-APERTURE OPTIMIZATION THAT INCLUDES FLUENCE-BASED SUB-OPTIMIZATION

(71) Applicant: Varian Medical Systems International AG, Steinhausen (CH)

(72) Inventors: Jarkko Y. Peltola, Tuusula (FI); Tuomas Tallinen, Helsinki (FI); Mikko Vainio, Espoo (FI)

(73) Assignee: Varian Medical Systems International AG, Steinhausen (CH)

(*) Notice: Subject to any disclaimer, the term of this patent is extended or adjusted under 35 U.S.C. 154(b) by 97 days.

(21) Appl. No.: 17/212,383

(22) Filed: Mar. 25, 2021

(65) Prior Publication Data
US 2022/0305287 A1    Sep. 29, 2022

(51) Int. Cl.
*A61N 5/10*    (2006.01)

(52) U.S. Cl.
CPC ......... *A61N 5/1031* (2013.01); *A61N 5/1045* (2013.01); *A61N 5/1048* (2013.01)

(58) Field of Classification Search
None
See application file for complete search history.

(56) References Cited

U.S. PATENT DOCUMENTS

2022/0088410 A1 * 3/2022 Hibbard ............... A61N 5/1081

OTHER PUBLICATIONS

Bedford, James; Treatment planning for volumetric modulated art therapy; Medical Physics, AIP, Melville, NY, US, vol. 36, No. 11, Oct. 9, 2009, pp. 5125-5138.
Bergman, Alanah, et al.; Direct aperture optimization for IMRT using Monte Carlo generated beamlets; Medical Physics, AIP, Melville, NY, US, vol. 33, No. 10, Sep. 14, 2006, pp. 3666-3679.
PCT Search Report and Written Opinion from related International Patent Application No. PCT/EP2022/057277; dated Jul. 19, 2022; 13 pages.

* cited by examiner

*Primary Examiner* — Hoon K Song
(74) *Attorney, Agent, or Firm* — Fitch, Even, Tabin & Flannery LLP

(57) ABSTRACT

After accessing optimization information for a particular patient and for a particular radiation treatment platform, a control circuit generates an optimized radiation treatment plan by processing the optimization information using direct-aperture-optimization that includes fluence-based sub-optimization. By one approach, the control circuit includes the fluence-based sub-optimization in at least some, but not necessarily all, iterations of the direct-aperture-optimization. By one approach, the control circuit is configured to include only a few iterations of the fluence-based sub-optimization when including the fluence-based sub-optimization in at least some, but not necessarily all, iterations of the direct-aperture-optimization.

15 Claims, 3 Drawing Sheets

METHOD AND APPARATUS TO FACILITATE GENERATING AN OPTIMIZED RADIATION TREATMENT PLAN USING DIRECT-APERTURE OPTIMIZATION THAT INCLUDES FLUENCE-BASED SUB-OPTIMIZATION

TECHNICAL FIELD

These teachings relate generally to treating a patient's planning target volume with energy pursuant to an energy-based treatment plan and more particularly to optimizing an energy-based treatment plan.

BACKGROUND

The use of energy to treat medical conditions comprises a known area of prior art endeavor. For example, radiation therapy comprises an important component of many treatment plans for reducing or eliminating unwanted tumors. Unfortunately, applied energy does not inherently discriminate between unwanted material and adjacent tissues, organs, or the like that are desired or even critical to continued survival of the patient. As a result, energy such as radiation is ordinarily applied in a carefully administered manner to at least attempt to restrict the energy to a given target volume. A so-called radiation treatment plan often serves in the foregoing regards.

A radiation treatment plan typically comprises specified values for each of a variety of treatment-platform parameters during each of a plurality of sequential fields. Treatment plans for radiation treatment sessions are often generated through a so-called optimization process. As used herein, "optimization" will be understood to refer to improving a candidate treatment plan without necessarily ensuring that the optimized result is, in fact, the singular best solution. Such optimization often includes automatically adjusting one or more treatment parameters (often while observing one or more corresponding limits in these regards) and mathematically calculating a likely corresponding treatment result to identify a given set of treatment parameters that represent a good compromise between the desired therapeutic result and avoidance of undesired collateral effects.

So-called direct-aperture optimization (DAO) comprises one known example in the foregoing regards.

Unfortunately, existing optimization techniques, including DAO, do not necessarily address all potential needs for all potential patients in all potential application settings. DAO, for example, may be too slow in some real-time application settings and/or may effectively lock up prematurely and/or may be (too) slow to react to external configuration changes such as changes to an objective function or application-setting geometry.

BRIEF DESCRIPTION OF THE DRAWINGS

The above needs are at least partially met through provision of the method and apparatus to facilitate generating an optimized radiation treatment plan using direct-aperture optimization that includes fluence-based sub-optimization described in the following detailed description, particularly when studied in conjunction with the drawings, wherein.

Figure 1:
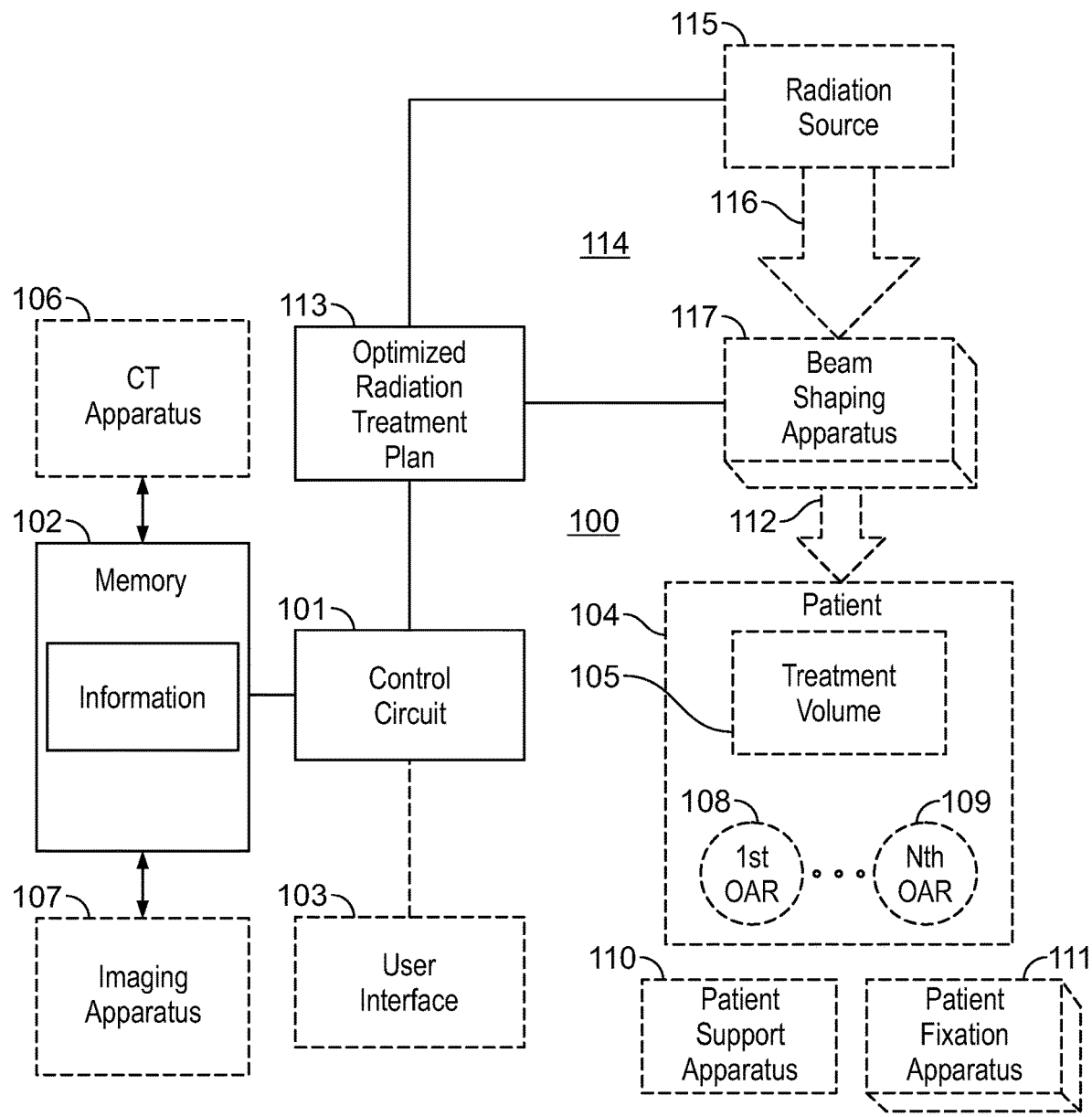
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein. The word "or" when used herein shall be interpreted as having a disjunctive construction rather than a conjunctive construction unless otherwise specifically indicated.

DETAILED DESCRIPTION

Generally speaking, these various embodiments serve to facilitate optimizing a patient treatment plan to administer therapeutic energy to a particular patient using a particular radiation treatment platform.

By one approach, these teachings provide for accessing optimization information for the particular patient and for the particular radiation treatment platform and then generating an optimized radiation treatment plan by, at least in part, optimizing a radiation treatment plan for the particular patient using the particular radiation treatment platform by, at least in part, processing the optimization information using direct-aperture-optimization that includes fluence-based sub-optimization. These teachings are highly flexible in practice and will accommodate various application settings. As one salient example, the radiation treatment plan can comprise a trajectory/arc plan.

By one approach, a control circuit carries out the foregoing optimization. This control circuit can be configured, if desired, to include the fluence-based sub-optimization in at least some, but not necessarily all, iterations of the direct-aperture-optimization. By one approach the control circuit is configured to include only a few iterations of the fluence-based sub-optimization when including the fluence-based sub-optimization in at least some, but not necessarily all, iterations of the direct-aperture-optimization. As one example in these regards, the control circuit can be configured to include those few iterations of the fluence-based sub-optimization such that a target fluence (as described herein) is refined by using a previous iteration target fluence as an initial fluence in a cost-gradient calculation as versus of fluence that was calculated from a then current multi-leaf collimator configuration.

Also if desired, the control circuit can be further configured to detect a change to at least one of at least one objective function corresponding to the direct-aperture-optimization and control point positioning corresponding to the direct-aperture-optimization, and in response to detecting that change, automatically include the fluence-based sub-optimization in at least one iteration of the direct-aperture-optimization.

By one approach the fluence-based sub-optimization comprises, at least in part and within a given iteration of the fluence-based sub-optimization, at least two of calculating an initial fluence from a given multi-leaf collimator configuration (i.e., a fluence that already exists when this sub-optimization begins as a loop within a direct-aperture-optimization iteration loop), then projecting a corresponding dose gradient onto a fluence plane to specify a gradient fluence, and then summing the initial fluence and the gradient fluence to thereby specify a target fluence. In such a case, and if desired, the control circuit can be configured to process the optimization information using the direct-aperture-optimization as a function of that specified target fluence.

So configured, a radiation treatment plan can be optimized using direct-aperture-optimization while avoiding at least some problems typically associated with direct-aperture-optimization and without necessarily increasing processing time requirements. The foregoing is especially true in arc/trajectory types of treatment, where control points are typically spread around large angular space and direct-aperture-optimization is used for a small section (such as an arc sector) of those control points. Instead, and in many application settings, a better result may be achievable in a reduced amount of processing time. The resultant optimized radiation treatment plan can of course then be utilized to apply therapeutic radiation to that particular patient via that particular radiation treatment platform.

These and other benefits may become clearer upon making a thorough review and study of the following detailed description. Referring now to the drawings, and in particular to FIG. 1, an illustrative apparatus 100 that is compatible with many of these teachings will first be presented.

In this particular example, the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

The control circuit 101 operably couples to a memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to information such as optimization information for a particular patient and information regarding a particular radiation treatment platform as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as a dynamic random access memory (DRAM).)

By one optional approach the control circuit 101 also operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

If desired the control circuit 101 can also operably couple to a network interface (not shown). So configured the control circuit 101 can communicate with other elements (both within the apparatus 100 and external thereto) via the network interface. Network interfaces, including both wireless and non-wireless platforms, are well understood in the art and require no particular elaboration here.

By one approach, a computed tomography apparatus 106 and/or other imaging apparatus 107 as are known in the art can source some or all of any desired patient-related imaging information.

In this illustrative example the control circuit 101 is configured to ultimately output an optimized energy-based treatment plan 113 (such as, for example, an optimized radiation treatment plan). This energy-based treatment plan 113 typically comprises specified values for each of a variety of treatment-platform parameters during each of a plurality of sequential exposure fields. In this case the energy-based treatment plan 113 is generated through an optimization process, examples of which are provided further herein.

By one approach the control circuit 101 can operably couple to an energy-based treatment platform 114 that is configured to deliver therapeutic energy 112 to a corresponding patient 104 in accordance with the optimized energy-based treatment plan 113. These teachings are generally applicable for use with any of a wide variety of energy-based treatment platforms/apparatuses. In a typical application setting the energy-based treatment platform 114 will include an energy source 115 such as a source of ionizing radiation.

By one approach this energy source 115 can be selectively moved via a gantry along an arcuate pathway (where the pathway encompasses, at least to some extent, the patient themselves during administration of the treatment). The arcuate pathway may comprise a complete or nearly complete circle as desired. By one approach the control circuit 101 controls the movement of the energy source 115 along that arcuate pathway, and may accordingly control when the energy source 115 starts moving, stops moving, accelerates, de-accelerates, and/or a velocity at which the energy source 115 travels along the arcuate pathway.

As one illustrative example, the energy source 115 can comprise, for example, a radio-frequency (RF) linear particle accelerator-based (linac-based) x-ray source, such as the Varian TrueBeam or Halcyon linear accelerator. The linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) 116 and high energy electrons.

A typical energy-based treatment platform 114 may also include one or more support apparatuses 110 (such as a couch) to support the patient 104 during the treatment session, one or more patient fixation apparatuses 111, a gantry or other movable mechanism to permit selective movement of the energy source 115, and one or more energy-shaping apparatuses 117 (for example, beam-shaping apparatuses such as jaws, multi-leaf collimators, and so forth) to provide selective energy shaping and/or energy modulation as desired.

In a typical application setting, it is presumed herein that the patient support apparatus 110 is selectively controllable to move in any direction (i.e., any X, Y, or Z direction) during an energy-based treatment session by the control circuit 101. As the foregoing elements and systems are well understood in the art, further elaboration in these regards is not provided here except where otherwise relevant to the description.

Figure 2:
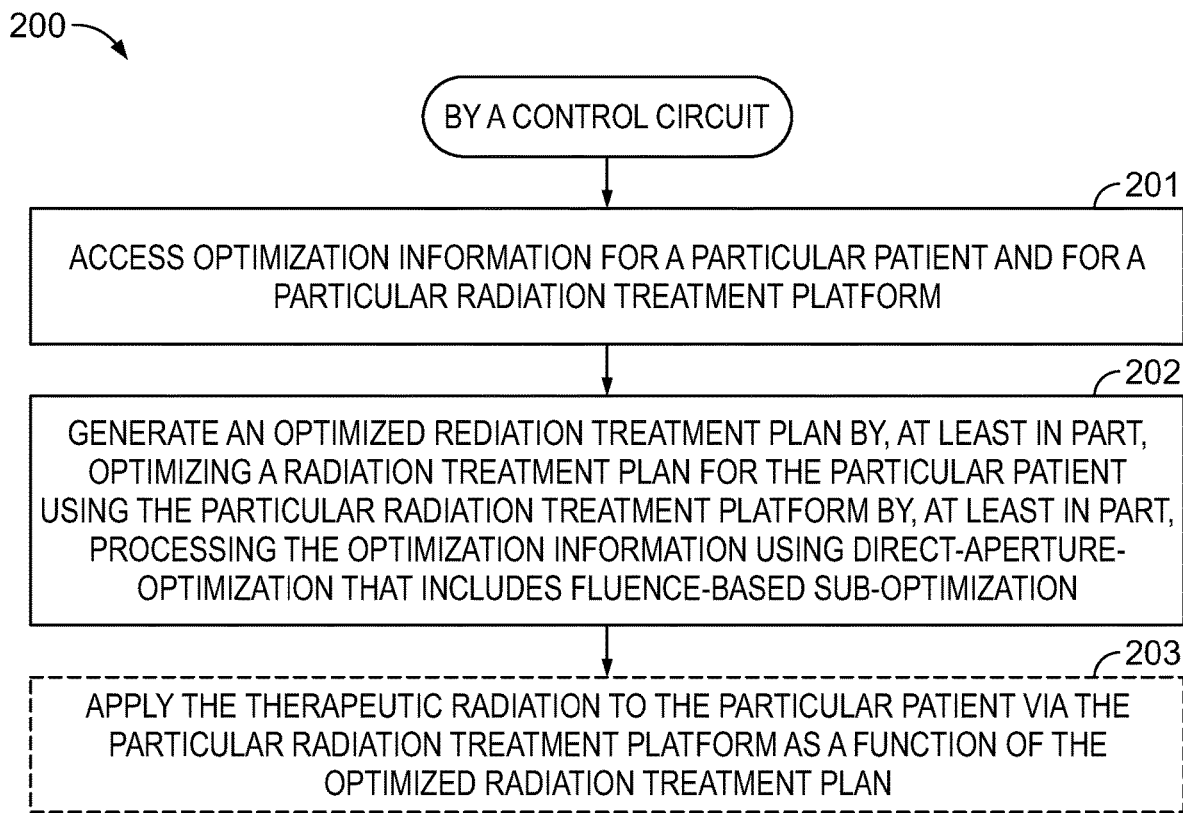
FIG. 2 comprises a flow diagram as configured in accordance with various embodiments of these teachings.

Referring now to FIG. 2, a process 200 that can be carried out, for example, in conjunction with the above-described application setting (and more particularly via the aforementioned control circuit 101) will be described. Generally speaking, this process 200 serves to facilitate generating an optimized radiation treatment plan 113 to thereby facilitate treating a particular patient with therapeutic radiation using a particular radiation treatment platform per that optimized radiation treatment plan.

At block 201, this process 200 can provide for the control circuit 101 accessing optimization information for the particular patient and for the particular radiation treatment platform. By one approach this comprises accessing the aforementioned memory 102. Optimization information comprises a relatively well understood area of prior art endeavor and accordingly further elaboration is not provided here in these regards for the sake of brevity.

At block 202, this process 200 then provides for generating an optimized radiation treatment plan by, at least in part, optimizing a radiation treatment plan for the particular patient using the particular radiation treatment platform by, at least in part, processing the optimization information using direct-aperture-optimization that includes fluence-based sub-optimization. Direct-aperture-optimization itself, of course, comprises a well understood area of prior art endeavor. Generally speaking, direct-aperture-optimization bypasses intensity optimization and instead directly optimizes the shapes and weights of the apertures of the beam shaping apparatus 117 (for example, the arrangement of the leaves of a multi-leaf collimator). Generally speaking, machine-dependent delivery constraints imposed by a beam-shaping apparatus 117 are enforced within the aperture optimization algorithm rather than in a separate leaf-sequencing step. Accordingly, leaf settings and aperture intensities are iteratively optimized simultaneously using, for example, a simulated annealing algorithm.

Per this process 200, this direct-aperture-optimization itself makes at least occasional use of fluence-based sub-optimization. More particularly, at least some, but not necessarily all, iterations of the direct-aperture-optimization process include, at least to a limited extent, fluence-based sub-optimization as well. By one approach, these teachings provide for using only a few iterations of the fluence-based sub-optimization when so including fluence-based sub-optimization. Fully converging on the corresponding cost function would typically require at least hundreds of iterations. By only using a few iterations, the fluence-based sub-optimization will most likely therefore not fully converge. The applicant has determined, however, that full convergence is not necessary to achieving desired performance results.

To achieve only a few iterations of the fluence-based sub-optimization process, by one approach the number of iterations may be set to a specific predetermined number, such as a number within the range of 5 to 10. By another approach, the number of iterations may be more dynamically determined. For example, the iterations may continue up to some maximum number (which maximum number may still represent only a "few" iterations, such as 25, 50, or 75) with earlier termination occurring when a current calculated result is less than (or equals) some predetermined threshold as compared to an initial value. Useful examples of a predetermined threshold are values ranging from 3% to 10%, with 5% likely being beneficial for many application settings.

So configured, the control circuit 101 can serve to include and make use of the foregoing few iterations of the fluence-based sub-optimization such that a target fluence is refined by using a previous iteration target fluence as an initial fluence in a cost gradient calculation as versus a fluence that was calculated from a current multi-leaf collimator configuration. More particularly, but without intending to suggest any limitations in these regards, the fluence-based sub-optimization can comprise, at least in part and within a given iteration of the fluence-based sub-optimization, first calculating an initial fluence from a given multi-leaf collimator configuration, and then projecting a corresponding dose gradient onto a fluence plane to thereby specify a gradient fluence. This process 200 can then sum the initial fluence and the gradient fluence to specify a corresponding target fluence. So configured, the control circuit 101 can then process the aforementioned optimization information using the direct-aperture-optimization as a function of that target fluence.

Figure 3:
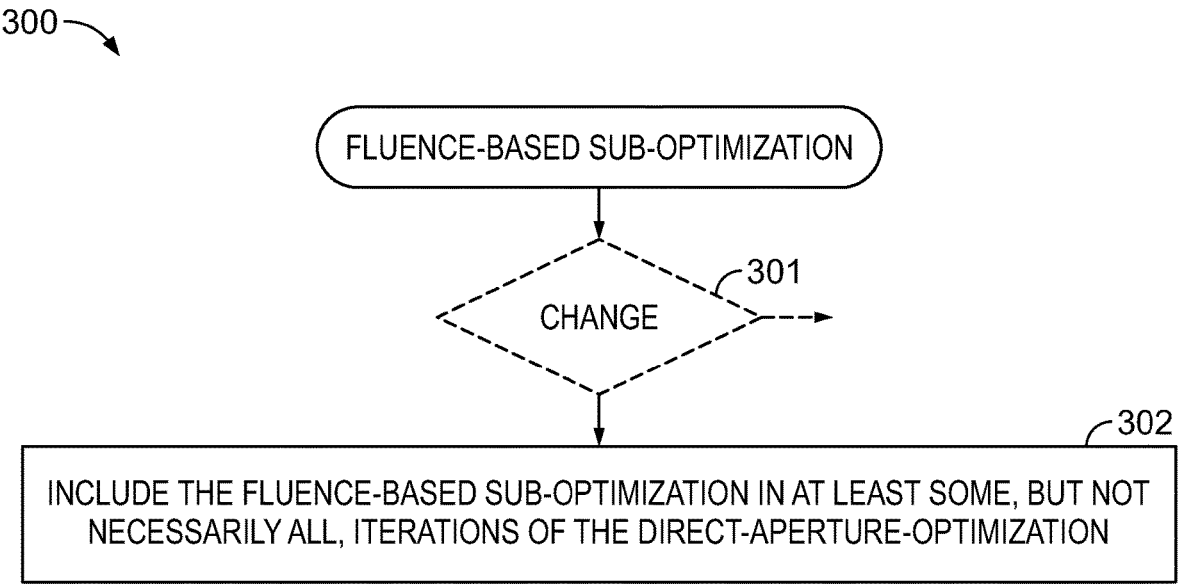
FIG. 3 comprises a flow diagram as configured in accordance with various embodiments of these teachings.

As noted above, this process 200 will accommodate including the fluence-based sub-optimization in at least some, but not necessarily all, iterations of the direct-aperture optimization. By one approach, the control circuit 101 can dynamically determine when to so utilize fluence-based sub-optimization. Referring momentarily to FIG. 3, an exemplary process 300 in these regards optionally provides for detecting, at block 301, when a change to a predetermined function or parameter occurs. This can comprise, for example, detecting a change to at least one objective function that corresponds to the direct-aperture-optimization. As another example, in lieu of the foregoing or in combination there with, this can comprise detecting a change to control point positioning as corresponds to the direct-aperture-optimization. (In the absence of detecting such a trigger event, this process 300 can accommodate any of a variety of responses. Examples of responses can include temporal multitasking (pursuant to which the control circuit 101 conducts other tasks before returning to again monitor for a trigger event) as well as continually looping back to essentially continuously monitor for the trigger event(s). These teachings also accommodate supporting this detection activity via a real-time interrupt capability.)

The foregoing optional approach can be particularly beneficial when there is a sudden large change in the cost function. Such may occur, for example, when optimization is running and there is already an existing leaf configuration, but there is a real-time need to presently alter the latter. This need can arise when a user changes the cost function, for example, or the geometry of the problem. This need can also present itself as input from another algorithm or some accessed database. As one salient example, a patient may already be lying on the treatment couch and their daily image may show that one or more relevant structures (such as a tumor or organ-at-risk) have changed somewhat such that the previous treatment plan needs to be adapted quickly before a scheduled treatment session can begin.

Upon detecting the predetermined change (or as is otherwise accommodated), this process 300 can then provide, at block 302, for responding by then automatically including the fluence-based sub-optimization in at least one iteration of the direct-aperture-optimization as described herein.

Figure 4:
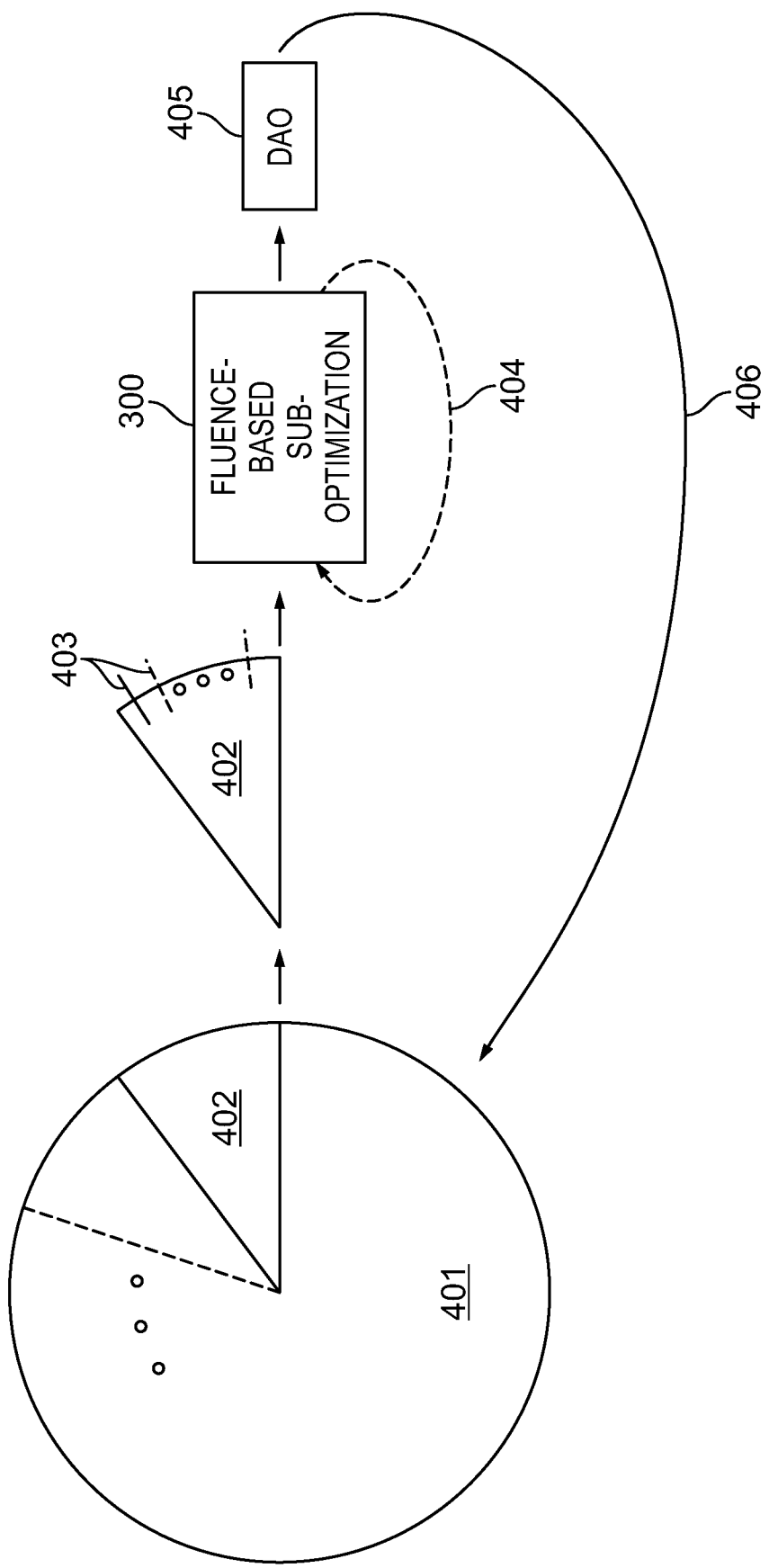
FIG. 4 comprises an illustrative schematic flow as configured in accordance with various embodiments of these teachings.

Referring again to FIG. 2 and also to FIG. 4 as well, a particular illustrative example will be provided in the foregoing regards. It will be understood that the details of this example are intended to serve an illustrative purpose and are not intended to suggest any particular limitations with respect to the practice of these teachings.

The circle 401 represents a 360° arc that corresponds to the gantry path and available positions for the aforementioned radiation source 115 during a radiation treatment session for a particular patient. To accommodate the calculations of direct-aperture-optimization this pathway is subdivided into sectors 402. Each sector 402, in turn, has one and typically many control points 403. For example, in a given application setting there may be 180 control points in a full 360° arc and each sector may have 16 such control points. The specifics of the foregoing are parameters that constitute at least a part of the optimization information for the particular radiation treatment platform 100. These are conventional aspects of a modern radiation treatment platform and accordingly further elaboration is not provided here for the sake of brevity.

In this example, and on a sector-by-sector basis, the control circuit 101 conducts fluence-based sub-optimization 300 for no more than a few iterations 404. As noted above, the foregoing activity can include determining an initial fluence and a gradient fluence that leads to determining a resultant new fluence. At block 405 direct-aperture-optimization is then utilized to find new leaf configurations for the corresponding control points 403 of the relevant sector 402 based upon that new fluence value. The direct-aperture-optimization accordingly finds a new, best total leaf configuration for all of the control points in this particular sector that will form the new fluence value. With a new iteration 406 this entire process can be repeated as appropriate.

By one approach, after all of the control point groups have been so processed, at least one additional optimization can be performed that finds a best combination of those configurations and which may alter the entire leaf-sequence and then proceed to a next iteration.

Those skilled in the art will appreciate that in this version of direct-aperture-optimization the iterative change to the optimized dose provides for, at initialization, using the leaf sequence defined in the control points to produce a certain fluence and determining the dose produced by that fluence. Iterating the above-described outer loop then provides for using that dose to determine a gradient fluence and hence a new target fluence that direct-aperture-optimization utilizes to determine a new leaf sequence which serves to then determine a new fluence based upon that new leaf sequence. A new dose is then calculated based upon that new fluence. When including the fluence-based sub-optimization inner loop in the foregoing process, a first iteration N can proceed as described above.

Iteration N+1 in this example then utilizes fluence-based sub-optimization to determine a gradient fluence from the available dose information and then a new target fluence from which a new dose is determined. The foregoing determination can be repeated for only a few times to yield a resultant new dose that serves as the input to the direct-aperture-optimization iteration N+2 (which can be similar or identical to iteration N described above). And of course the forgoing cycles can be repeated in accordance with the iterative processing of the direct-aperture-optimization approach.

So configured, these teachings provide for much faster assessment of new doses and can create fluence trade-offs all around the arc before searching for particular leaf configurations. As noted above, these teachings can be particularly helpful in the presence of sudden large changes to cost functions. That said, these teachings can also be beneficial even in the absence of changes to the cost function because the search inherent to direct-aperture-optimization can, in practice, become stagnant and use of these teachings can effectively reinvigorate the direct-aperture-optimization search activity.

Referring again to FIG. 2, at optional block 203 these teachings will accommodate then applying therapeutic radiation to the particular patient 104 via the particular radiation treatment platform 114 as a function of the optimized radiation treatment plan 113 that results from the foregoing processes. The use of such an apparatus/platform in such a matter constitutes a well-understood area of prior art endeavor and therefore is not described here in more detail.

Those skilled in the art will recognize that a wide variety of modifications, alterations, and combinations can be made with respect to the above-described embodiments without departing from the scope of the invention. Accordingly, such modifications, alterations, and combinations are to be viewed as being within the ambit of the inventive concept.

What is claimed is:

1. A method to facilitate treating a particular patient with therapeutic radiation using a particular radiation treatment platform per an optimized radiation treatment plan, the method comprising:

by a control circuit:

accessing optimization information for the particular patient and for the particular radiation treatment platform;

generating the optimized radiation treatment plan by, at least in part, optimizing a radiation treatment plan for the particular patient using the particular radiation treatment platform by, at least in part, processing the optimization information using direct-aperture-optimization that includes fluence-based sub-optimization by including only a few iterations of the fluence-based sub-optimization in at least some, but not necessarily all, iterations of the direct-aperture-optimization, such that a target fluence is refined by using a previous iteration target fluence as an initial fluence in a cost-gradient calculation as versus a fluence that was calculated from a current multi-leaf collimator configuration.

2. The method of claim 1 wherein the control circuit is further configured to:
   detect a change to at least one of at least one objective function corresponding to the direct-aperture-optimization and control point positioning corresponding to the direct-aperture-optimization;
   in response to detecting the change, automatically including the fluence-based sub-optimization in at least one iteration of the direct-aperture-optimization.

3. The method of claim 1 further comprising:
   applying the therapeutic radiation to the particular patient via the particular radiation treatment platform as a function of the optimized radiation treatment plan.

4. A method to facilitate treating a particular patient with therapeutic radiation using a particular radiation treatment platform per an optimized radiation treatment plan, the method comprising:
   by a control circuit:
      accessing optimization information for the particular patient and for the particular radiation treatment platform;
      generating the optimized radiation treatment plan by, at least in part, optimizing a radiation treatment plan for the particular patient using the particular radiation treatment platform by, at least in part, processing the optimization information using direct-aperture-optimization that includes fluence-based sub-optimization; wherein the fluence-based sub-optimization comprises, at least in part and within a given iteration of the fluence-based sub-optimization, at least two of:
         calculating an initial fluence from a given multi-leaf collimator configuration;
         projecting a corresponding dose gradient onto a fluence plane to specify a gradient fluence;
         summing the initial fluence and the gradient fluence to specify a target fluence.

5. The method of claim 4 wherein the control circuit is configured to process the optimization information using the direct-aperture-optimization as a function of the target fluence.

6. An apparatus to facilitate treating a particular patient with therapeutic radiation using a particular radiation treatment platform per an optimized radiation treatment plan, the apparatus comprising:
   a memory having optimization information for the particular patient and for the particular radiation treatment platform stored therein;
   a control circuit operably coupled to the memory and being configured to:
      access the optimization information for the particular patient and for the particular radiation treatment platform;
      generate the optimized radiation treatment plan by, at least in part, optimizing a radiation treatment plan for the particular patient using the particular radiation treatment platform by, at least in part, processing the optimization information using direct-aperture-optimization that includes fluence-based sub-optimization by, at least in part and within a given iteration of the fluence-based sub-optimization, at least two of:
         calculating an initial fluence from a given multi-leaf collimator configuration;
         projecting a corresponding dose gradient onto a fluence plane to specify a gradient fluence;
         summing the initial fluence and the gradient fluence to specify a target fluence.

7. The apparatus of claim 6 wherein the control circuit is configured to include the fluence-based sub-optimization in at least some, but not necessarily all, iterations of the direct-aperture-optimization.

8. The apparatus of claim 7 wherein the control circuit is further configured to:
   detect a change to at least one of at least one objective function corresponding to the direct-aperture-optimization and control point positioning corresponding to the direct-aperture-optimization;
   in response to detecting the change, automatically including the fluence-based sub-optimization in at least one iteration of the direct-aperture-optimization.

9. The apparatus of claim 7 wherein the control circuit is configured to include only a few iterations of the fluence-based sub-optimization when including the fluence-based sub-optimization in at least some, but not necessarily all, iterations of the direct-aperture-optimization.

10. The apparatus of claim 6 wherein the control circuit is configured to process the optimization information using the direct-aperture-optimization as a function of the target fluence.

11. The apparatus of claim 6 wherein the control circuit is configured to include the fluence-based sub-optimization in at least some, but not necessarily all, iterations of the direct-aperture-optimization.

12. The apparatus of claim 11 wherein the control circuit is further configured to:
   detect a change to at least one of at least one objective function corresponding to the direct-aperture-optimization and control point positioning corresponding to the direct-aperture-optimization;
   in response to detecting the change, automatically including the fluence-based sub-optimization in at least one iteration of the direct-aperture-optimization.

13. The apparatus of claim 11 wherein the control circuit is configured to include only a few iterations of the fluence-based sub-optimization when including the fluence-based sub-optimization in at least some, but not necessarily all, iterations of the direct-aperture-optimization.

14. An apparatus to facilitate treating a particular patient with therapeutic radiation per an optimized radiation treatment plan, the apparatus comprising:
   a particular radiation treatment platform;
   a memory having optimization information for the particular patient and for the particular radiation treatment platform stored therein;
   a control circuit operably coupled to the memory and being configured to:
      access the optimization information for the particular patient and for the particular radiation treatment platform;
      generate the optimized radiation treatment plan by, at least in part, optimizing a radiation treatment plan for the particular patient using the particular radiation treatment platform by, at least in part, processing the optimization information using direct-aperture-optimization that includes fluence-based sub-optimization, wherein the fluence-based sub-optimization comprises, at least in part and within a given iteration of the fluence-based sub-optimization, at least two of:

calculating an initial fluence from a given multi-leaf collimator configuration;

projecting a corresponding dose gradient onto a fluence plane to specify a gradient fluence;

summing the initial fluence and the gradient fluence to specify a target fluence.

15. The apparatus of claim 14 wherein the control circuit is configured to process the optimization information using the direct-aperture-optimization as a function of the target fluence.

\* \* \* \* \*